United States Patent
Navarro Fernandez et al.

(10) Patent No.: US 10,689,329 B2
(45) Date of Patent: Jun. 23, 2020

(54) TERT-AMINE CORE-BEARING ACYRLAMIDES AND ADHESIVE FORMULATIONS

(71) Applicant: OREGON HEALTH & SCIENCE UNIVERSITY, Portland, OR (US)

(72) Inventors: Oscar Navarro Fernandez, Tigard, OR (US); Carmem Pfeifer, Beaverton, OR (US); Ana Paula Piovezan Fugolin, Portland, OR (US); Jack Ferracane, Beaverton, OR (US)

( * ) Notice: Subject to any disclaimer, the term of this patent is extended or adjusted under 35 U.S.C. 154(b) by 0 days.

(21) Appl. No.: 16/361,764

(22) Filed: Mar. 22, 2019

(65) Prior Publication Data

US 2019/0292136 A1    Sep. 26, 2019

Related U.S. Application Data

(60) Provisional application No. 62/646,855, filed on Mar. 22, 2018.

(51) Int. Cl.
| | | |
|---|---|---|
| C08F 2/46 | (2006.01) | |
| C08F 2/50 | (2006.01) | |
| C08G 61/04 | (2006.01) | |
| C07C 233/38 | (2006.01) | |
| C09J 133/26 | (2006.01) | |
| A61K 6/30 | (2020.01) | |
| A61K 6/887 | (2020.01) | |

(52) U.S. Cl.
CPC .............. *C07C 233/38* (2013.01); *A61K 6/30* (2020.01); *A61K 6/887* (2020.01); *C09J 133/26* (2013.01)

(58) Field of Classification Search
None
See application file for complete search history.

(56) References Cited

U.S. PATENT DOCUMENTS

| | | | |
|---|---|---|---|
| 9,668,944 B2 | 6/2017 | Stelzig et al. | |
| 2015/0231040 A1 | 8/2015 | Stelzig et al. | |
| 2015/0335535 A1* | 11/2015 | Klee | A61K 6/0023 |
| | | | 523/118 |
| 2017/0296441 A1 | 10/2017 | Renn et al. | |
| 2017/0296442 A1* | 10/2017 | Renn | A61K 6/0052 |

FOREIGN PATENT DOCUMENTS

EP    3124477 A1    1/2017

OTHER PUBLICATIONS

Moszner et al., Monomers for Adhesive Polymers, 4a Synthesis and Radical Polymerization of Hydrolytically Stable Crosslinking Monomers, Macromol. Mat. Eng., 2003, 288, pp. 621-628.
Moszner et al., Bis-(acrylamide)s as new cross-linkers for resin-based composite restoratives, Dental Materials, 22, 2006, pp. 1157-1162.
Catel et al., Synthesis of acidic vinylcyclopropanes for dental applications, Polym Int 2017, 66, pp. 1410-1417.
Schuster et al., Photopolymers for Rapid Prototyping of Soluble Mold Materials and Molding of Cellular Biomaterials, Monatshefte fur Chemie, 137, pp. 843-853, 2006.
Moraes et al., Improved Dental Adhesive Formulations Based on Reactive Nanogel Additives, Journal of Dental Research 91(2): 179-184.
Tjaderhane et al., Strategies to prevent hydrolytic degradation of the hybrid layer—A review, (2013). Dental Materials 29(10): 999-1011.
Szaloki et al., Preparation of reactive polymeric nanoparticles (RPNPs), (2008). Colloid and Polymer Science 286(4): 435-444.

* cited by examiner

*Primary Examiner* — Jessica Whiteley (57) ABSTRACT

The present invention provides tertiary amine core-bearing acrylamides and their use in adhesive formulations, particularly including dental adhesives.

13 Claims, 2 Drawing Sheets

TERT-AMINE CORE-BEARING ACYRLAMIDES AND ADHESIVE FORMULATIONS

This invention was made with government support under Grant Nos. U01DE023756 and R01 DE026113 awarded by the National Institutes of Health. The government has certain rights in the invention.

The present invention is in the field of tertiary amine core-bearing acrylamides, particularly including their use in adhesive formulations.

BACKGROUND OF THE INVENTION

Methacrylamide monomers have been used in a variety of adhesive compositions, including for orthopedic and dental uses. Dental adhesives are widely used in restorative dentistry to provide retention of the filling materials, creating a bond between the dental material and the hard tissues in the tooth, dentin and enamel. For its application, an acidic etching of the tooth surface creates micropores filled with a mixture of acrylic and/or methacrylic monomers, a photo-initiator system and solvent. The addition of inorganic particles that modulate and improve physical and mechanical properties is also becoming increasingly common. Depending on whether the acidic conditioning of the tooth is done with an acid or with an acidic monomer, the adhesive is classified as "etch & rinse" or "self-etching".

2-hydroxyethyl methacrylate (HEMA) is one of the most ubiquitous monomers in dental adhesive systems due to its ability to dissolve other higher molecular weight crosslinking monomers, such as bisphenol A glycidyl dimethacrylate (Bis-GMA) or urethane dimethacrylates (UDMA). However, HEMA's hydrophilicity promotes hydrolytic degradation of the polymer network, since the ester bonds of methacrylates hydrolyze under acidic aqueous conditions. In addition, they are known to have allergenic potential and have a considerable level of cytotoxicity. For these reasons, the development of alternatives to its use has been the subject of numerous studies.

SUMMARY OF THE INVENTION

Provided herein are acrylamide monomer compounds useful in adhesive compositions, the compounds comprising Formula (I):

wherein:
$R_1$ and $R_2$ are independently $C_1$-$C_4$ alkyl;
$R_3$ is selected from $C_1$-$C_4$ alkyl and a group of the formula:

n is an integer selected from 0 and 1;
n1, n2, and n3 are each independently integers selected from the group of 2, 3, and 4; and
$R_4$ is $C_1$-$C_4$ alkyl;
with the proviso that, when n=0, the sum of n1+n2 is 3, 5, or 7.

In the formula defining one option for $R_3$, above, the wavy line to the left of $(CH_2)_{n3}$ represents the bond through which the $R_3$ formula would be bound to the central nitrogen atom of Formula (I).

Also provided are polymeric alkylacrylamide monomers and methods for producing them.

Also provided are adhesive compositions comprising:
 a) a first alkylacrylamide monomer comprising a compound of Formula (I), as defined above, or N,N'-(propane-1,3-diyl)bis(N-ethylacrylamide) (DAAP);
 b) a polymerizable bifunctionalized methacrylate base monomer;
 c) a polymerization initiator; and
 d) a polymerization inhibitor or a polymerization stabilizer.

DETAILED DESCRIPTION OF THE INVENTION

Also provided herein are monomer compounds comprising Formula (I), wherein n1, n2, and n3 are each independently integers selected from 2 and 3, and $R_1$, $R_2$, $R_3$, and $R_4$ are as defined above.

Also provided herein are monomer compounds comprising Formula (I), wherein n1, n2, and n3 are each independently integers selected from 3 and 4, and $R_1$, $R_2$, $R_3$, and $R_4$ are as defined above.

Also provided herein are monomer compounds comprising Formula (I), wherein n1, n2, and n3 are each 2 and $R_1$, $R_2$, $R_3$, and $R_4$ are as defined above.

Further provided herein are monomer compounds comprising Formula (I), wherein n1, n2, and n3 are each 3 and $R_1$, $R_2$, $R_3$, and $R_4$ are as defined above.

Additionally provided herein are monomer compounds comprising Formula (I), wherein n1, n2, and n3 are each 4 and $R_1$, $R_2$, $R_3$, and $R_4$ are as defined above.

Provided are compounds monomer compounds comprising Formula (I), wherein n1 and n2 are each independently integers selected from the group of 2, 3, and 4; and $R_1$, $R_2$, and $R_3$, are each independently $C_1$-$C_4$ alkyl.

Provided are compounds monomer compounds comprising Formula (I), wherein n1 and n2 are each independently integers selected from the group of 2, 3, and 4; and $R_1$, $R_2$, and $R_3$, are each independently $C_1$-$C_3$ alkyl.

Provided are compounds monomer compounds comprising Formula (I), wherein n1 and n2 are each independently integers selected from the group of 2, 3, and 4; and $R_1$, $R_2$, and $R_3$, are each independently $C_1$-$C_2$ alkyl.

Provided are compounds monomer compounds comprising Formula (I), wherein n1 and n2 are each independently integers selected from the group of 2, 3, and 4; and $R_1$, $R_2$, and $R_3$, are each methyl.

Provided are compounds monomer compounds comprising Formula (I), wherein n1 and n2 are each independently integers selected from the group of 2 and 3; and $R_1$, $R_2$, and $R_3$, are each methyl.

Provided are compounds monomer compounds comprising Formula (I), wherein n1 and n2 are each independently integers selected from the group of 2, 3, and 4; and $R_1$, $R_2$, and $R_3$, are each ethyl.

Provided are compounds monomer compounds comprising Formula (I), wherein n1 and n2 are each independently integers selected from the group of 2 and 3; and $R_1$, $R_2$, and $R_3$, are each ethyl.

For each embodiment or description herein defining compounds of Formula (I), there is an equally defined embodiment or description defining compounds wherein n=1, as indicated by Formula (Ia):

(Ia)

Also provided are compounds of Formula (II):

(II)

wherein:
$R_1$, $R_2$, and $R_1$ are each independently $C_1$-$C_4$ alkyl; and
n1, n2, and n3 are each independently integers selected from the group of 2, 3, and 4.

Additionally provided are compounds of Formula (II), wherein $R_1$, $R_2$, and $R_1$ are each independently $C_1$-$C_4$ alkyl; and n1, n2, and n3 are each independently integers selected from 2 and 3.

Additionally provided are compounds of Formula (II), wherein $R_1$, $R_2$, and $R_1$ are each independently $C_1$-$C_4$ alkyl; and n1, n2, and n3 are each independently integers selected from 3 and 4.

Additionally provided are compounds of Formula (II), wherein $R_1$, $R_2$, and $R_1$ are each independently $C_1$-$C_4$ alkyl; and n1, n2, and n3 are each 2.

Additionally provided are compounds of Formula (II), wherein $R_1$, $R_2$, and $R_1$ are each independently $C_1$-$C_4$ alkyl; and n1, n2, and n3 are each 3.

Also provided are compounds of Formula (II), wherein $R_1$, $R_2$, and $R_1$ are each independently $C_1$-$C_4$ alkyl; and n1, n2, and n3 are each 4.

Additionally provided are compounds of Formula (II), wherein $R_1$, $R_2$, and $R_1$ are each independently $C_1$-$C_3$ alkyl; and n1, n2, and n3 are each independently integers selected from the group of 2, 3, and 4.

Further provided are compounds of Formula (II), wherein $R_1$, $R_2$, and $R_1$ are each independently $C_1$-$C_2$ alkyl; and n1, n2, and n3 are each independently integers selected from the group of 2, 3, and 4.

Further provided are compounds of Formula (II), wherein $R_1$, $R_2$, and $R_4$ are each independently $C_1$-$C_2$ alkyl; and n1, n2, and n3 are 2.

Further provided are compounds of Formula (II), wherein $R_1$, $R_2$, and $R_4$ are each independently $C_1$-$C_2$ alkyl; and n1, n2, and n3 are 3.

Further provided are compounds of Formula (II), wherein $R_1$, $R_2$, and $R_4$ are each independently $C_1$-$C_2$ alkyl; and n1, n2, and n3 are 4.

Further provided are compounds of Formula (II), wherein $R_1$, $R_2$, and $R_4$ are each methyl; and n1, n2, and n3 are each independently integers selected from the group of 2, 3, and 4.

Further provided are compounds of Formula (II), wherein $R_1$, $R_2$, and $R_4$ are each methyl; and n1, n2, and n3 are each independently integers selected from the group of 2 and 3.

Further provided are compounds of Formula (II), wherein $R_1$, $R_2$, and $R_4$ are each ethyl; and n1, n2, and n3 are each independently integers selected from the group of 2, 3, and 4.

Further provided are compounds of Formula (II), wherein $R_1$, $R_2$, and $R_4$ are each ethyl; and n1, n2, and n3 are each independently integers selected from the group of 2 and 3.

Acrylamide monomers herein may be produced using methods known in the art, exemplified by the schemes below:

Also provided are methods for preparing alkyl acrylamide compounds of varying polymeric complexity that may be used as acrylamide monomers in adhesive compositions or for other uses. The reaction scheme below, which may be carried out at room temperature. Terminal secondary alkyl amines as depicted by Formula (III) in which $R_1$, $R_2$, and $R_3$ represent the $C_1$-$C_4$ alkyl groups from Formula (I), may be treated with MeCN and acryloyl chloride to produce the corresponding bis-alkyl acrylamides represented by corresponding Formula (I)) in which $R_1$, $R_2$, and $R_3$ are $C_1$-$C_4$ alkyl. A specific example of the process if further exemplified by the preparation of N,N'-((methylazanediyl)bis(propane-3,1-diyl))bis(N-methylacrylamide) from N1,N3-dimethyl-N1-(3-(methylamino)propyl)propane-1,3-diamine.

Provided are additional processes for preparing alkyl acrylamide monomers of increasing polymeric complexity. The initial step of preparing compounds of Formula (I) and other Formulas herein may be seen as beginning with multiple cores, including the three below:

For the sake of brevity, the synthetic discussions herein will center on reactions involving core iii), above, but it is understood that each of the reaction steps is contemplated using cores i) and ii) and that their steps and reaction products are understood and part of the disclosure herein.

In one embodiment compounds of Formula (III) may be reacted with methyl acrylate and methanol to form bis-methyl esters of Formula (IV) in which $R_1$, $R_2$, and $R_3$ are $C_1$-$C_4$ alkyl. A specific example is the preparation of dimethyl 3,3'-(((methylazanediyl)bis(propane-3,1-diyl))bis(methylazanediyl))dipropionate from N1,N3-dimethyl-N1-(3-(methylamino)propyl)propane-1,3-diamine.

The methyl esters of Formula (IV) can then be reacted with N,N-dimethylethylenediamine to product methylamine compounds of Formula (V), such as 3,3'-(((methylazanediyl)bis(propane-3,1-diyl))bis(methylazanediyl))bis(N-methyl-N-(2-(methylamino)ethyl)propanamide).

Compounds of Formula (V) can then be reacted with acryloyl chloride and acetonitrile to prepare alkyl acrylamide compounds of Formula (VI):

(V)

(IV)

(VI)

(VII)

Following the specific examples above, Formula (VI) may be represented by N,N'-(3,7,11,15,19-pentamethyl-4,18-dioxo-3,7,11,15,19-pentaazahenicosane-1,21-diyl)bis(N-methylacrylamide).

In Formulas (IV), (V), and (VI), as well as other formulas below, the wavy line indicates that the structure to the right of the wavy line mirrors that seen to the left of —(CH$_2$)— on the left side of the structure. For example, the complete structure of Formula (IV) is understood to be:

(IV)

In another step of monomer polymerization, compounds of Formula (IV) may be reacted with a monoprotected diamine, such as BOC-protected tert-butyl (2-(methylamino)ethyl)carbamate, to prepare terminal amines of Formula (VII), such as 3,3'-(((methylazanediyl)bis(propane-3,1-diyl))bis(methylazanediyl))bis(N-(2-aminoethyl)-N-methylpropanamide)

The reaction scheme above shows the use of tert-butyl (2-(methylamino)ethyl)carbamate to provide the amine terminus of Formula (VII) and such steps are referenced in comparable stages of dendrimer formation. It is understood that that additional amine spacer groups may be used in this step, including 4-(aminomethyl)piperidine, piperidin-4-amine, $N^1$-methylethane-1,2-diamine, $N^1$-ethylethane-1,2-diamine, $N^1$-propylethane-1,2-diamine, $N^1$-butylethane-1,2-diamine, $N^1$-methylpropane-1,3-diamine, $N^1$-ethylpropane-1,3-diamine, $N^1$-propylpropane-1,3-diamine, and $N^1$-butylpropane-1,3-diamine. The corresponding compounds and groups of compounds utilizing each of these spacers in understood in the steps herein.

The terminal amines of Formula (VII) may then be converted to the corresponding dimethyl 3,3'-azanediyl-diproprionate of Formula (VIII), which in turn may be converted using N1,N1-dimethylethane-1,2-diamine to the corresponding 3,3'-azanediylbis(N-methyl-N-(2-(methylamino)ethyl)propanamide) compound of Formula (IX).

(XII)

(XIII)

(VII)

(VIII)

(IX)

Formula (VIII) may be represented by dimethyl 4,26-bis(3-methoxy-3-oxopropyl)-7,11,15,19,23-pentamethyl-8,22-dioxo-4,7,11,15,19,23,26-heptaazanonacosanedioate and Formula (IX) by 3,3',3'',3'''-((3,7,11,15,19-pentamethyl-4,18-dioxo-3,7,11,15,19-pentaazahenicosane-1,21-diyl)bis(azanetriyl))tetrakis(N-methyl-N-(2-(methylamino)ethyl)propanamide).

Compounds of Formula (IX) may then be reacted with acryloyl chloride and MeCN (room temperature) to form acrylamides of Formula (X):

(X)

A corresponding example of a compound of Formula (X) is:

Also provided herein is a process for preparing serially extended acrylamide monomers using sequential steps of treating an ester compound of Formula (IV) of (a) treating the ester with a monoprotected diamine in the presence of methanol at around 40° C. to form a terminal amine as seen above in the preparation of compounds of Formula (VII), followed by (b) reacting the terminal amine with methyl acrylate in the presence of methanol to form the next corresponding ester, as accomplished in forming compounds of Formula (VIII).

In this sequence, compounds of Formula (IV) can be used to form compounds of Formula (XI):

(XI)

which in turn can be used to form corresponding esters of Formula (XII).

(XII)

Corresponding repetitions of the (a)-(b) sequence of (a) treating the ester with a monoprotected diamine in the presence of methanol at around 40° C. to form a terminal amine as seen above in the preparation of compounds of Formula (VII), followed by (b) reacting the terminal amine with methyl acrylate in the presence of methanol to form the next corresponding ester may be accomplished to add polymeric links to the structure, followed by treatment of the final ester compound with N,N-dimethylethylenediamine in the presence of methanol (40° C.) to form the next corresponding secondary amine, which may then be treated with acryloyl chloride in the presence of methanol to form a final acrylamide monomer.

As noted above, herein are provided adhesive compositions comprising:
 a) a first monomer comprising a compound of Formula (I), as defined above;
 b) a polymerizable bifunctionalized methacrylate base monomer;
 c) a polymerization initiator; and
 d) a polymerization inhibitor or a polymerization stabilizer.

Also provided are adhesive compositions comprising:
 a) a first monomer comprising a compound of Formula (II), as defined above;
 b) a polymerizable bifunctionalized methacrylate base monomer;
 c) a polymerization initiator; and
 d) a polymerization inhibitor or a polymerization stabilizer.

One embodiment herein provides adhesive compositions comprising:
 a) a first monomer comprising a compound of Formula (I), as defined above, the first monomer comprising 30-50 wt % of the composition;
 b) a polymerizable bifunctionalized methacrylate base monomer comprising 50-70 wt % of the composition;
 c) a polymerization initiator; and
 d) a polymerization inhibitor or a polymerization stabilizer.

One embodiment herein provides adhesive compositions comprising:
 a) a first monomer comprising a compound of Formula (I), as defined above, the first monomer comprising 35-45 wt % of the composition;
 b) a polymerizable bifunctionalized methacrylate base monomer comprising 55-65 wt % of the composition;
 c) a polymerization initiator; and
 d) a polymerization inhibitor or a polymerization stabilizer.

One embodiment herein provides adhesive compositions comprising:
 a) a first monomer comprising a compound of Formula (I), as defined above, the first monomer comprising about 40 wt % of the composition;
 b) a polymerizable bifunctionalized methacrylate base monomer comprising about 60 wt % of the composition;
 c) a polymerization initiator; and
 d) a polymerization inhibitor or a polymerization stabilizer.

One embodiment herein provides adhesive compositions comprising:
 a) a first monomer comprising a compound of Formula (II), as defined above, the first monomer comprising 30-50 wt % of the composition;
 b) a polymerizable bifunctionalized methacrylate base monomer comprising 50-70 wt % of the composition;
 c) a polymerization initiator; and
 a polymerization inhibitor or a polymerization stabilizer One embodiment herein provides adhesive compositions comprising:
 a) a first monomer comprising a compound of Formula (II), as defined above, the first monomer comprising 35-45 wt % of the composition;
 b) a polymerizable bifunctionalized methacrylate base monomer comprising 55-65 wt % of the composition;
 c) a polymerization initiator; and
 d) a polymerization inhibitor or a polymerization stabilizer.

One embodiment herein provides adhesive compositions comprising:
 a) a first monomer comprising a compound of Formula (II), as defined above, the first monomer comprising about 40 wt % of the composition;
 b) a polymerizable bifunctionalized methacrylate base monomer comprising about 60 wt % of the composition;
 c) a polymerization initiator; and
 d) a polymerization inhibitor or a polymerization stabilizer A further embodiment provides adhesive compositions comprising:

a) N,N'-(propane-1,3-diyl)bis(N-ethylacrylamide) (DAAP) comprising 30-50 wt % of the composition;
b) a polymerizable bifunctionalized methacrylate base monomer comprising 50-70 wt % of the composition;
c) a polymerization initiator; and
d) a polymerization inhibitor or a polymerization stabilizer.

A further embodiment provides adhesive compositions comprising:
a) N,N'-(propane-1,3-diyl)bis(N-ethylacrylamide) (DAAP) comprising 35-45 wt % of the composition;
b) a polymerizable bifunctionalized methacrylate base monomer comprising 55-65 wt % of the composition;
c) a polymerization initiator; and
d) a polymerization inhibitor or a polymerization stabilizer.

A further embodiment provides adhesive compositions comprising:
a) N,N'-(propane-1,3-diyl)bis(N-ethylacrylamide) (DAAP) comprising about 40 wt % of the composition;
b) a polymerizable bifunctionalized methacrylate base monomer comprising about 60 wt % of the composition;
c) a polymerization initiator; and
d) a polymerization inhibitor or a polymerization stabilizer.

Examples of methacrylate base monomers that may be used in the adhesive compositions herein include:

Also useful in the combinations herein are polyethylene glycol bis-methacrylates of the formula:

wherein n is an integer from 1 to 12.

Examples of poly(propylene glycol)dimethacrylate compounds useful in the combinations are those of the formula:

Wherein:
m is an integer of from 1 to 10;
n is an integer from 1 to 10; and
m+n is no greater than 15.

One example of poly(propylene glycol)dimethacrylates is poly(propylene glycol)(400) dimethacrylate (PPGDMA 400), wherein m+n=7.

((propane-2,2-diylbis(4,1-phenylene))bis(oxy))bis(2-hydroxypropane-3,1-diyl) bis(2-methylacrylate) (BisGMA)

m + n = 3
BisEMA

7,7,9-trimethyl-4,13-dioxo-3,14-dioxa-5,12-diazahexadecane-1,16-diyl bis(2-methylacrylate) (UDMA) and 1p;1p 7,9-dimethyl-4,13-dioxo-3,14-dioxa-5,12-diazahexadecane-1,16-diyl bis(2-methylacrylate)

Examples of polyethylene glycol bis-methacrylates include:

ethane-1,2-diyl bis(2-methylacrylate)

oxybis(ethane-2,1-diyl) bis(2-methylacrylate)

(ethane-1,2-diylbis(oxy))bis(ethane-2,1-diyl) bis(2-methylacrylate) (TEGDMA)

Also useful in the combinations herein are alkylene bis-acrylates of the formula:

wherein:
n is an integer from 2 to 12; and
X is selected from hydrogen and $C_1$-$C_4$ alkyl.
Examples of alkylene bis-acrylates include:

1,10-decanediol dimethacrylate 2-methyl-1,8-octanediol dimethacrylate 1,6-hexanediol dimethacrylate    and butane-1,3-diyl bis(2-methylacrylate)

The term "polymerizable bifunctionalized methacrylate base monomer" as used herein refers to a substantially linear molecule comprising acrylate or alkylacrylate groups at each end capable of forming an adhesive resin with compounds of Formula (I).

The term "initiator" or "polymerization initiator" herein refers to thermal initiating, redox-initiating, and/or photoinitiating compounds capable of inducing polymerization throughout a significant depth of composite material, such as camphorquinone (CQ); trimethylbenzoyl-diphenyl-phosphine oxide (TPO); Ethyl-4-dimethylamino benzoate (EDMAB); 2,2-Dimethoxy-2-phenylacetophenone (DMPA); Bisacylphosphine oxide (BAPO); 1-Phenyl-1,2-propanedione (PPD); phosphine oxide compounds, including naphthacene (APO), 9-anthracene (APO), and bisacylphosphine oxide (BAPO); 1-phenyl-1,2-propanedione (PPD); thioxanthone (TX) and its derivatives; dibenzoyl germanium derivatives, such as benzoyltrimethylgermane (BTG) and dibenzoyldiethylgermane; hexaarylbiimidazole derivatives; silane based derivatives; (diethylgermanediyl) bis((4-methoxyphenyl)methanone) (Ivocerin); benzenesulfinic acid sodium salt (BS); diaryliodonium salts (such as diphenyliodonium chloride or iodonium salt [diphenyliodonium hexafluorophosphate (DPIHP or DPI-PF6))], bromide, iodide, or hexafluorophosphate; and benzoyl peroxide (BPO). It is understood that in the compositions herein, one initiator material may be used or 2 or more may be used, such as the combination of camphorquinone with a co-initiator, such as a tertiary amine initiator (such as ethyl-4-(dimethylamino) benzoate (EDMAB) and/or 2-(dimethylamino)ethyl methacrylate (DMAEMA)), or a combination of DMPA/DPI-PF6, CQ/PPD, CQ/DMAEMA, CQ/EDMAB, CQ/DMAEMA/PDIHP, or CQ/EDMAB/DPIHP.

The terms "polymerization inhibitor" and "polymerization stabilizer" for use in the adhesive composites herein include butylated hydroxytoluene, butylhydroxytoluene, or 2,6-di(tert-butyl)-4-methylphenol (BHT); tert-butyl hydroquinone (TBHQ); 2,5-di-tert-butylhydroquinone (DTBHQ); monomethyl ether hydroquinone (MEHQ); 3,5-di-tert-butyl-4-hydroxyanisole (2,6-di-tert-butyl-4-ethoxyphenol); 2,5-di-tert-butyl hydroquinone; 2-(2'-hydroxy-5'-methylphenyl)-2H-benzotriazole; 2-(2'-hydroxy-5'-t-octylphenyl)-2H-benzotriazole; 2-hydroxy4-methoxybenzophenone (UV-9); 2-(2'-hydroxy-4',6'-di-tertpentylphenyl)-2H-benzotriazole; 2-hydroxy-4-n-octoxybenzophenone; and 2-(2'-hydroxy-5'-methacryloxyethylphenyl)-2H-benzotriazole.

In different embodiments the compositions herein for dental use may further comprise a filler or dental filler material. The terms "filler" or "dental filler" herein refer to glass filler particles useful as dental fillers in composites, including silica materials, glass fillers, alkaline glass fillers, metal oxides, and prepolymerized fillers. Conventional and commercially available fillers for use in the present compositions include silica oxides (silicon dioxide), aluminum oxide, titanium dioxide, zinc oxide, zirconium oxide, calcium oxide, phosphorus oxides, barium glass, strontium glass, quartz, barium aluminum silicate glass, barium borosilicate, lithium aluminum silicate, strontium aluminum silicate glass, and silicon dioxide.

Also optionally, the adhesive compositions may comprise a solvent, such as selected from water, ethanol, acetone, or combinations thereof.

The term "alkyl" refers to a straight or branched hydrocarbon. A $C_1$-$C_4$ alkyl group includes methyl, ethyl, n-propyl, isopropyl, n-butyl, s-butyl, isobutyl, and t-butyl groups.

Specific compounds used herein include:

Materials and Methods

Materials

Figure 1:
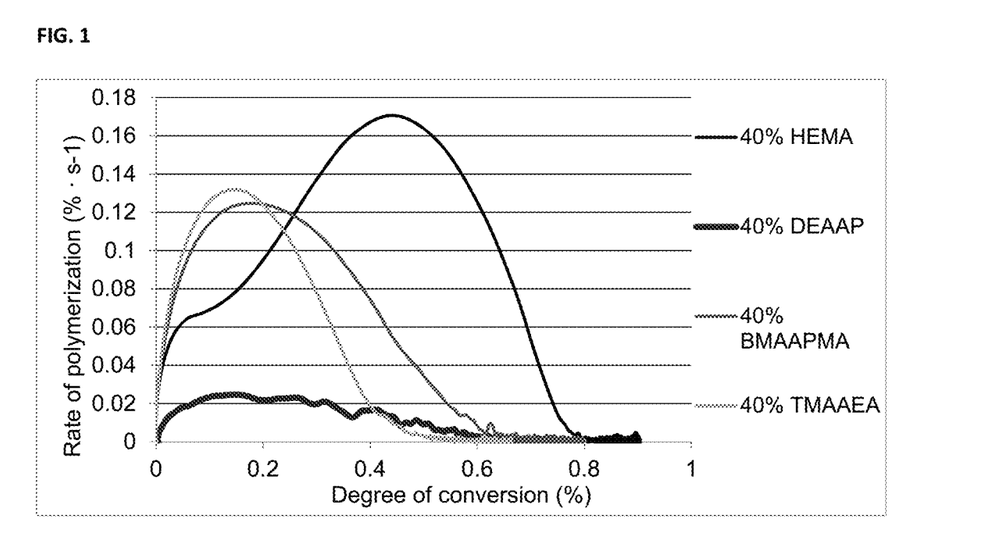
FIG. 1 provides a comparison of polymerization kinetics (rate of polymerization and degree of conversion) for compositions comprising 40% of the cited monomers and 60% UDMA.
Figure 2:
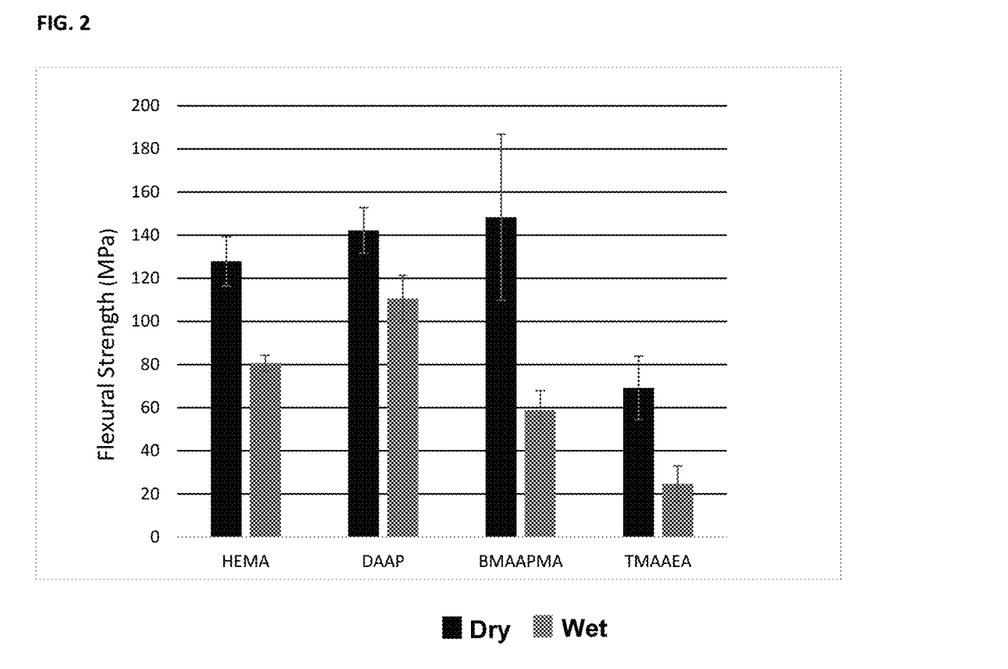
FIG. 2 depicts the mechanical properties of wet and dry flexural strength for the four adhesive compositions.
Figure 3:
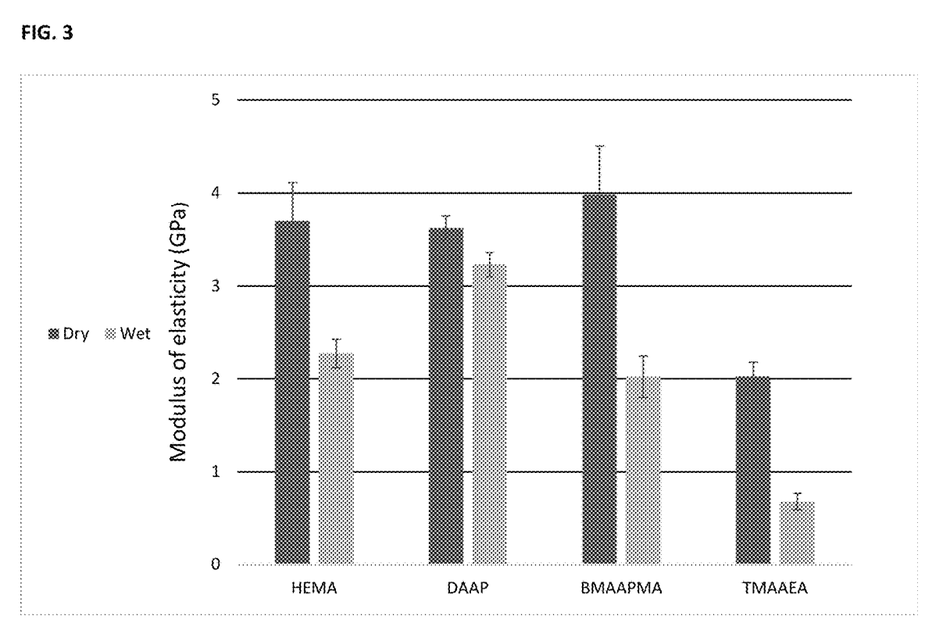
FIG. 3 depicts the mechanical properties of wet and dry modulus of elasticity for the four adhesive compositions.
Figure 4:
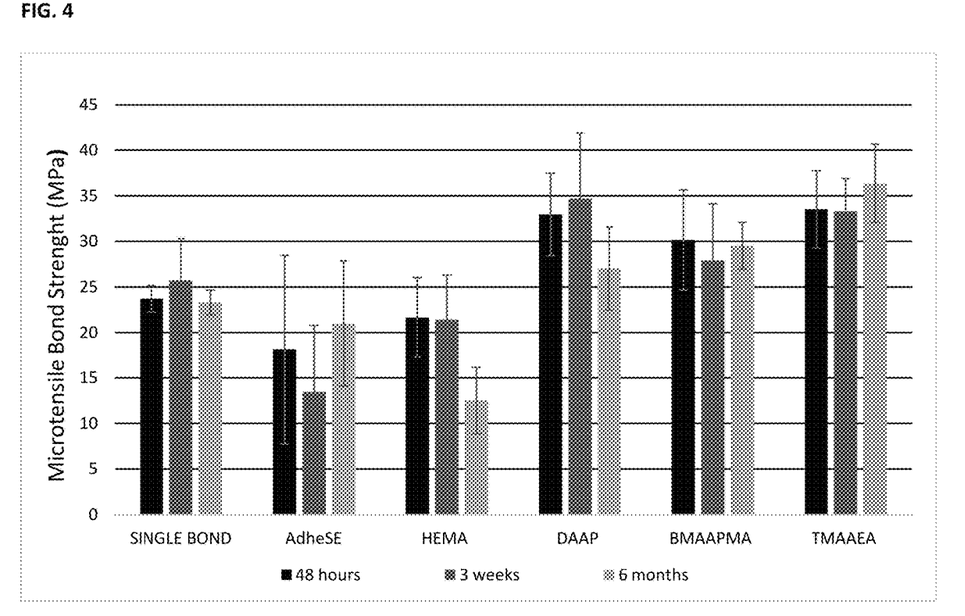
FIG. 4 depicts the microtensile bond strength demonstrated by the cited compositions after 24 hours, 3 weeks, and 6 months storage in water.

The monomers UDMA and HEMA (FIG. 1) were used as received (ESSTECH Inc, Essington, Pa.). Reagents for the synthesis of DAAP, BMAAPMA and TMAAEA (FIG. 1) were used as received unless otherwise noted (Sigma-Aldrich, St. Louis, Mo., USA). Acetonitrile (ACS grade) was dried over 3 Å molecular sieves for at least 24 h prior to use.

Methods

Syntheses: General considerations. Reactions were carried out in anhydrous MeCN and on a blanket on $N_2$. Acryloyl chloride was freshly distilled before use. $^1H$ and $^{13}C$ NMR spectra were acquired with a Bruker 400 MHz Avance II+ spectrometer (Bruker Co., Billerica, Mass., USA). N,N-Diethyl-1,3-bis(acrylamido)propane (DAAP) was synthesized following a literature procedure (Catel et al., Polymer International 62(12) 2013: pp. 1717-1728).

N,N-Bis[(3-methylaminoacryl)propyl]methylamine (BMAAPMA): Acryloyl chloride (90 mmol, 7.35 mL) and MEHQ (3 mg) were added to a 500 mL round bottom flask equipped with a magnetic stir bar, and dissolved in 150 mL of MeCN. The flask was placed in a −5° C. bath and an addition funnel containing N,N-bis[3-(methylamino)propyl] methylamine (90 mmol, 15.6 g) dissolved in 45 mL of MeCN was attached. The amine solution was then added dropwise and the reaction allowed to stir for 48 h. The insoluble solid formed (amine.HCl salt) was filtered out and the liquid portion concentrated in vacuo. The remaining oil was redissolved in DCM and washed in turn with 0.1 N HCl aqueous solution, saturated $NaHCO_3$ aqueous solution and water. The remaining organic layer was dried over $MgSO_4$ and filtered, followed by solvent removal in vacuo, yielding 6.985 g of a slightly yellow oil (24.8 mmol, 45% yield). $^1H$ NMR ($D_2O$): δ 6.66-6.57 (m, 2H), 6.08-6.02 (m, 2H), 5.70 (dt, J=13.2, 1.7 Hz, 2H), 3.36 (dtd, J=22.2, 7.2, 1.8 Hz, 4H), 3.02 (d, J=0.8 Hz, 3H), 2.88 (s, 3H), 2.35-2.27 (m, 4H), 2.14-2.10 (m, 3H), 1.74-1.62 (m, 4H). $^{13}C$ NMR{H} ($D_2O$): δ 168.9, 128.3, 127.5, 53.5, 53.1, 48.4, 46.2, 40.8, 35.6, 33.9, 24.7, 23.3. ITMS m/z Calcd ($C_{15}H_{28}N_3O_2^+$): 282.22; experimental 282.21.

Tris[(2-methylaminoacryl)ethyl]amine (TMAAEA): Acryloyl chloride (39.83 mmol, 3.25 mL) and MEHQ (1 mg) were added to a 250 mL round bottom flask equipped with a magnetic stir bar, and dissolved in 75 mL of MeCN. The flask was placed in a −5° C. bath and an addition funnel containing tris[2-(methylamino)ethyl]amine (26.55 mmol, 5 g) dissolved in 20 mL of MeCN was attached. The amine solution was then added dropwise and the reaction allowed to stir for 48 h. The insoluble solid formed (amine.HCl salt) was filtered out and the liquid portion concentrated in vacuo. The remaining oil was redissolved in DCM and washed in turn with 0.1 N HCl aqueous solution, saturated $NaHCO_3$ aqueous solution and water. The remaining organic layer was dried over $MgSO_4$ and filtered, followed by solvent removal in vacuo, yielding 3.052 g of a colourless oil (8.71 mmol, 66% yield). $^1H$ NMR ($D_2O$): δδ 6.60-6.57 (m, 3H), 6.11-6.04 (m, 3H), 5.74-5.70 (m, 3H), 3.51-3.40 (m, 6H), 3.06-2.89 (m, 9H), 2.73-2.63 (m, 6H). $^{13}C$ NMR{H} ($D_2O$): 168.9, 128.3, 127.4, 51.6, 50.0, 47.96, 45.5, 36.0, 34.3. ITMS m/z Calcd ($C_{18}H_{31}N_4O_3^+$): 351.24; experimental 351.23.

ITMS m/z Calcd ($C_{18}H_{31}N_4O_3^+$): 351.24; experimental 351.23.

Mechanical Tests and Kinetics of Polymerization

Kinetics of polymerization was followed in real-time using near-IR, as described previously by Stansbury and Dickens, Dental Materials, 17(1):2001, pp. 71-79. Briefly, materials were placed in a rubber mold (5 mm in diameter and 0.8 mm in thickness) sandwiched between two glass slides. The assembly is inserted on the chamber of a infrared spectrometer (Nicolet 6700, ThermoFisher Scientific, Madison, Wis., USA) and the vinyl overtone peak at 6165 $cm^{-1}$ is followed while the material is photoactivated at 350 mW/cm2 for 5 min. Degree of conversion in real time is calculated as the percentage vinyl bonds remaining in relation to the initial peak area. The rate of polymerization is derived from the conversion vs. time curve.

Flexural strength and modulus were determined in bar specimens measuring 2×2×25 mm, produced in a similar fashion to what was described for the kinetics of polymerization test. Bars were stored either dry or in water at room temperature for one week and tested in three point bending, as prescribed in ISO 4049.

Hydrolytic degradation. Aqueous solutions with pH=1 were prepared using deuterium oxide ($D_2O$, pH 9.8) and adjusted by adding DCl (20 w/w % in $D_2O$). 1.2 mL, 60 mM solutions of each monomer were prepared at each pH value (n=3), and stored at 37° C. for 1 month.

Microtensile bond strength tests were conducted as described by Sadek et al., Journal of Adhesive Dentistry, 7(4): 2005, pp. 297-302.

Recently extracted caries-free human third molars (n=6) had the cusps removed to expose a flat dentin surface. This study was approved by the Oregon Health & Science University IRB (#1RB00012056). The dentin surface was etched with 35% phosphoric acid (3M ESPE, St. Paul, Minn., USA) for 15 s, rinsed and blotted dry. The adhesive materials were applied in two consecutive coats, photoactivated for 20 s. For this test only, three commercial adhesives were also tested: Adper Single Bond (3M-ESPE), Clearfil SE Bond (Kuraray, Tokyo, Japan) and AdheSE (Ivoclar-Vivadent, Schaan, Liechestein). A block of composite (Filtek Supreme, A2, 3M-ESPE) was built in 2 increments with 2 mm thickness, photoactivated for 20 s each at 700 mW/cm² (Demi Plus, Dentsply-Sirona, Milford, Del., USA). The restored teeth were stored for 24 h in distilled water, then sectioned to produce 1×1 mm² sticks. The sticks were then stored for an additional 24 h or 3 weeks in distilled water at 37° C., and then tested in tension (0.5 mm/min) until failure to determine microtensile bond strength using a custom-made jig (Odeme equipamentos, Luzerna, S.C., Brazil) attached to a universal testing machine (Criterion, MTS, Eden Prairie, Minn., USA).

Selected groups were also tested after storing the sticks for 6 months in distilled water at 37° C.

What is claimed:
1. A compound of Formula (II):

(II)

wherein:
R₁, R₂, and R₄ are each independently $C_1$-$C_4$ alkyl; and
n1, n2, and n3 are each independently integers selected from the group of 2, 3, and 4.

2. The compound of claim 1 wherein n1, n2, and n3 are each independently integers selected from 2 and 3.

3. The compound of claim 1 wherein n1, n2, and n3 are each independently integers selected from 3 and 4.

4. A compositions comprising:
a) a first monomer comprising a compound of claim 1
b) a polymerizable bifunctionalized methacrylate base monomer;
c) a polymerization initiator; and
d) a polymerization inhibitor or a polymerization stabilizer.

5. The composition of claim 4 comprising:
a) a first monomer comprising a compound claim 1 wherein the first monomer comprises 30-50 wt % of the composition;
b) a polymerizable bifunctionalized methacrylate base monomer comprising 50-70 wt % of the composition;
c) a polymerization initiator; and
d) a polymerization inhibitor or a polymerization stabilizer.

6. The composition of claim 1 comprising:
a) a first monomer comprising a compound of claim 1 wherein the first monomer comprises 35-45 wt % of the composition;
b) a polymerizable bifunctionalized methacrylate base monomer comprising 55-65 wt % of the composition;
c) a polymerization initiator; and
d) a polymerization inhibitor or a polymerization stabilizer.

7. The composition of claim 4 comprising:
a) a first monomer comprising a compound of claim 1 wherein the first monomer comprises about 40 wt % of the composition;
b) a polymerizable bifunctionalized methacrylate base monomer comprising about 60 wt % of the composition;
c) a polymerization initiator; and
d) a polymerization inhibitor or a polymerization stabilizer.

8. The composition of claim 4, wherein the polymerizable bifunctionalized methacrylate base monomer is selected from the group of:
((propane-2,2-diylbis(4,1-phenylene))bis(oxy))bis(2-hydroxypropane-3,1-diyl)bis(2-methylacrylate) (Bis-GMA);
7,7,9-trimethyl-4,13-dioxo-3,14-dioxa-5,12-diazahexadecane-1,16-diyl bis(2-methylacrylate) (UDMA); and
(ethane-1,2-diylbis(oxy))bis(ethane-2,1-diyl)bis(2-methylacrylate) (TEGDMA).

9. The composition of claim 7, wherein the first monomer is N,N-Diethyl-1,3-bis(acrylamido)propane.

10. The composition of claim 4, wherein the polymerization initiator is one or more agents selected from the group of camphorquinone (CQ); trimethylbenzoyl-diphenyl-phosphine oxide (TPO); Ethyl-4-dimethylamino benzoate (EDMAB); 2,2-Dimethoxy-2-phenylacetophenone (DMPA); Bisacylphosphine oxide (BAPO); 1-Phenyl-1,2-propanedione (PPD); phosphine oxide compounds, including naphthacene (APO), 9-anthracene (APO), and bisacylphosphine oxide (BAPO); 1-phenyl-1,2-propanedione (PPD); thioxanthone (TX) and its derivatives; a dibenzoyl germanium derivative, benzoyltrimethylgermane (BTG), dibenzoyldiethylgermane; hexaarylbiimidazole derivatives; a silane based derivative; (diethylgermanediyl)bis((4-methoxyphenyl)methanone); benzenesulfinic acid sodium salt (BS); a diaryliodonium salt, diphenyliodonium chloride or iodonium salt [diphenyliodonium hexafluorophosphate (DPIHP or DPI-PF6))], bromide, iodide, or hexafluorophosphate; and benzoyl peroxide (BPO).

11. The composition of claim 4, wherein the polymerization initiator is a combination selected from the group of camphorquinone/ethyl-4-(dimethylamino)benzoate (EDMAB), camphorquinone/2-(dimethylamino)ethyl methacrylate (DMAEMA)), DMPA/DPI-PF6, CQ/PPD, CQ/DMAEMA, CQ/EDMAB, CQ/DMAEMA/PDIHP, or CQ/EDMAB/DPIHP.

12. The composition of claim 4, further comprising a solvent selected from water, ethanol, acetone, or combinations thereof.

13. The composition of claim 4, further comprising a dental filler material.

\* \* \* \* \*